United States Patent
Narayan et al.

(10) Patent No.: US 7,367,995 B2
(45) Date of Patent: May 6, 2008

(54) BIODIESEL ADDITIVE AND METHOD OF PREPARATION THEREOF

(75) Inventors: Ramani Narayan, Okemos, MI (US); Daniel Graiver, Midland, MI (US); Kenneth W. Farminer, Midland, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 160 days.

(21) Appl. No.: 11/363,193

(22) Filed: Feb. 27, 2006

(65) Prior Publication Data

US 2006/0194975 A1    Aug. 31, 2006

Related U.S. Application Data

(60) Provisional application No. 60/656,679, filed on Feb. 28, 2005.

(51) Int. Cl.
*C10L 1/12* (2006.01)

(52) U.S. Cl. .................. 44/457; 554/156; 554/157; 554/169

(58) Field of Classification Search ................ 44/457; 554/156, 157, 169
See application file for complete search history.

(56) References Cited

U.S. PATENT DOCUMENTS 6,488,727 B2 *  12/2002  Naegeli et al. ............... 44/457

* cited by examiner

*Primary Examiner*—Yvonne Eyler
*Assistant Examiner*—Yate' K Cutliff
(74) *Attorney, Agent, or Firm*—Ian C. McLeod

(57) ABSTRACT

Fuel oxygenates comprised of fatty acid or fatty acid ester derivatives which have been reacted with ozone; a base; and a lower alkanol (1 to 8 carbon atoms) are described. The oxygenates comprise ester groups at a point of cleavage by the ozone which provide oxygen in the oxygenate.

10 Claims, No Drawings

BIODIESEL ADDITIVE AND METHOD OF PREPARATION THEREOF

CROSS-REFERENCE TO RELATED APPLICATIONS

This application claims priority to provisional Application Ser. No. 60/656,679, filed Feb. 28, 2005.

STATEMENT REGARDING FEDERALLY SPONSORED RESEARCH OR DEVELOPMENT

Not Applicable

STATEMENT REGARDING GOVERNMENT RIGHTS

Not Applicable

BACKGROUND OF THE INVENTION (1) Field of the Invention

The present invention relates to motor fuel additives as an oxygenated fuel having relatively high oxygen content to improve the burning characteristics of the fuel. More specifically, the present invention is related to an oxygenated fuel additive for improving the cetane number of a middle distillate diesel fuel and its impact on total hydrocarbon exhaust emissions, without adversely affecting the storage stability, lubrication, water shedding properties or corrosion characteristics of the fuel.

(2) Description of Related Art

The cetane number of a middle distillate diesel fuel is a measure of the ignition quality of the fuel. Usually, fuels having a low cetane number are characterized by long ignition delays, increased combustion noise and even misfiring.

The term cetane number, similar to the term octane number, refers to a combustion characteristic of the fuel in an internal combustion engine. Cetane number represents the ability of the fuel base to self-ignite in the combustion chamber of the engine. An excessively low cetane number corresponds to an excessively long self-ignition delay, which results in late, violent and incomplete combustion with the formation of non-combusted residues. This poor combustion is reflected by an increase in the polluting emissions in the exhaust and a corresponding increase in the noise due to self-ignition of the fuel. This poor combustion is particularly notable when the engine is idling and when starting the engine, in particular in cold weather. It is therefore preferable, in order for diesel engines to operate well, to have available a fuel, which exhibits a high cetane number.

It is well known that motor vehicle emissions are the primary source of ambient carbon monoxide levels in most areas. To address this problem, the use of oxygenated fuel was mandated under the Clean Air Act Amendments of 1990 in order to increase the combustion efficiency of the fuel, thereby reducing the emissions in areas that did not meet the Federal ambient air standard for carbon monoxide. One method gasoline marketers are using to comply with the Clean Air Act Amendments is to change the hydrocarbon composition of the fuel by blending middle distillates having low cetane numbers with other feedstocks having a higher cetane rating or by hydrotreating the middle distillate to thereby improve the cetane rating. An alternative method is to enhance the oxygen content of the fuel by admixing it with octane enhancing oxygenates.

By definition, oxygenates are organic compounds containing hydrogen, carbon and oxygen. Consequently, the addition of oxygen to a hydrocarbon-only fuel results in a change in the proportion of fuel to air that is required to provide complete combustion of the fuel to water and carbon dioxide. The exact air-to-fuel ratio needed for complete combustion of fuel is called its "stoichiometric air-fuel ratio". This ratio is about 14.7 pounds of air to one pound of fuel (14.7:1) for nonoxygenated gasoline. Since less air is required for oxygenated fuel, less air per pound of fuel is required and the effect of this type of fuel change on an engine is called "enleanment". This enleanment effect due to oxygenates is similar in magnitude to operating an engine at 5-15° F. lower ambient temperatures where the higher air density enleans the air-fuel mixture.

The Clean Air Act requires that the fuel to contain at least 2.7% oxygen and this level of oxygen is typically achieved by the addition of about 15% by weight methyl tertiary butyl ether (MTBE) or about 7.5% ethanol (by volume). Other fuel oxygenates that are in use to a lesser extent, or that may potentially be used, include ethyl tertiary-butyl ether (ETBE), tertiary-amyl methyl ether (TAME), diisopropyl ether (DIPE), and tertiary-butyl alcohol (TBA). Fuel oxygenates, especially MTBE and ethanol, also are used to enhance the octane of conventional gasoline. However, many of these oxygenates led to acute health symptoms and subsequent possible health risks associated with using oxygenated fuels. Although they generally decrease pollutants such as benzene and 1,3-butadiene, they tend to increase the emissions of aldehydes (acetaldehyde from use of ethanol or ETBE and formaldehyde from use of MTBE). Furthermore, concerns related to reduced fuel economy, engine performance, as well as contamination of drinking ground water by non-biodegradable oxygenates have also been documented.

The alkyl ether oxygenates, which are most commonly used oxygenates at the present time, are well known in the prior art. For example, U.S. Pat. No. 5,001,292 to Harandi et al. describes a process for reducing the cost of producing MTBE and other alkyl t-butyl ethers by converting unreacted hydrocarbons and alkanols from the etherification process to fuel having the desired boiling range hydrocarbons. The oxygenate components can be blended into gasoline separately as described in U.S. Pat. No. 4,468,233 to Bruderreck et al. whereby a t-butyl ether containing motor fuel composition including MTBE and isopropyl t-butyl ether (i-PTBE) and sec-butyl t-butyl ether (s-BTBE) is said to provide a high octane number, reduced emissions and improved solubility. However, these alkyl ether-based compounds are known to be much less biodegradable than ethanol or aromatic hydrocarbons and, therefore, they tend to persist longer in ground water. Even more worrisome is the fact that they are adsorbed only weakly into the soil and consequently, move with the ground-water flow and migrate over long distances away from the initial point of contamination. Exhaust emissions from vehicles and evaporative losses from fueling stations are the primary sources of oxygenate release to the atmosphere. As these alkyl ether fuel oxygenates tend to persist in the atmosphere for days to weeks and because of their low water solubility, they accumulate in air. Hence, they provide a non-point, low concentration source to the hydrologic cycle as a result of the dispersive effect of weather patterns and occurrence in precipitation.

The other class of common oxygenates are ethanol and other low molecular alcohols. These oxygenates-blended fuels are particularly sensitive to poor handling and storage practices because of the possibility of phase separation due to their high water solubility. It is imperative that water must be removed from fuel tanks and fuel lines to prevent water absorption and subsequent phase separation. Water has a higher density than the fuel, so upon phase separation a water phase will be formed as a layer below the fuel. Because water does not burn, and since the fuel intake in most engines is at, or near, the bottom of the fuel tank, most engines will not run once phase separation occurs. The situation is even more serious in small engines that require that oil be mixed with the gasoline. In this case, if phase separation occurs, the alcohol/water phase may separate with the oil, thus removing the oil from the gasoline. If the engine is able to run on the remaining gasoline, damage could result from insufficient lubrication.

Other oxygen containing additives as oxygenates have also been disclosed in the prior art. For example, U.S. Pat. No. 2,912,313 to Hinkamp et al. discloses that the addition of both a peroxide and a dihalo compound produces a synergistic increase in the cetane number. The use of peroxides is also disclosed in U.S. Pat. No. 2,472,152 to Farkus et al. which describes a method for improving the cetane number of middle distillates by oxidation of saturated cyclic hydrocarbon or the naphthenic hydrocarbons to form naphthenic peroxides. This patent suggests that the oxidation may be accelerated in the presence of an oil-soluble metal salt as an initiator and is preferably carried out in the presence of an inorganic base. However, the naphthenic peroxides that formed as well as other peroxides are known deleterious gum initiators. Consequently, gum inhibitors such as phenols, cresols and cresyic acids, which are toxic and carcinogenic, must be added to the oxidized material to reduce or prevent gum formation.

U.S. Pat. No. 4,494,961 to Venkat further discloses the preparation of oxygenates by mild oxidation of raw, untreated, highly aromatic, middle distillate fractions having a low hydrogen content by contacting the fraction at a temperature from 50-350° C. in the presence of a catalyst which is either (i) an alkaline earth metal permanganate, (ii) an oxide of a metal of Groups IB, IIB, IIIB, IVB, VB, VIIB, VIIB or VIIIB of the periodic table, or a mixture of (i) and (ii). European Patent Application 0 252 606 A2 also relates to improving cetane number of a middle distillate fuel fraction which may be hydro-refined by contacting the fraction with oxygen or oxidant, in the presence of catalytic metals such as tin, antimony, lead, bismuth and transition metals of Groups IB, IIB, VB, VIIB, VIIB and VIIIB of the periodic table, preferably as an oil-soluble metal salt. This application states that the catalyst selectively oxidizes benzylic carbon atoms in the fuel to ketones.

German Patent No. 3,136,030 discloses that the cetane number of dialkoxyalkanes can be increased by partial oxidation with ozone or hydrogen peroxide and U.S. Pat. No. 6,488,727 to Naegeli discloses a method of producing oxygenated fuel by introducing oxygen gas into the base fuel, which is then heated using a sparging process. Another oxidation process is described in U.S. Pat. No. 6,673,230 to Hagen wherein a mixture of organic compounds derived from petroleum is selectively oxygenated by a hydrogen peroxide and/or alkylhydroperoxide, an aliphatic monocarboxylic acid of 2 to 6 carbon atoms, water and a heterogeneous oxygenation catalyst system preferably comprises of chromium molybdate or bismuth molybdate and optionally magnesium.

A partial biobased oxygenates mixture is claimed in U.S. Pat. No. 5,308,365 to Kesling where a glycerol-based oxygenate mixture was obtained by the addition of an olefin, such as isobutene to glycerol to yield dialkylated and trialkylated glycerol derivatives. Similar glycerol ethers are also claimed in Patent JP 07018271. Glycerol acetals are disclosed in U.S. Pat. No. 6,890,364 to Delfort. Accordingly, the glycerol acetals are prepared by reaction of an aldehyde or a ketone and glycerol or by a transacetalization reaction under acidic conditions. However, these and other similar compounds of the prior art, have a major disadvantage related to their high hydrophilic nature, which promotes the trapping of water in the fuels. Another disadvantage of many of the oxygenated compounds in the prior art is related to their multi-stage manufacturing method, which makes them expensive and limits their continuous manufacture on a large scale.

Only a few esters have been evaluated as oxygenates due to the relatively high cost of production and separation associated with this process. However, it was shown by Beuther and Kobylinski (Proceeding of the Symposium on Chemistry of Oxygenates in Fuels, American Chemical Society, Kansas City meeting 1982) that both isopropyl acetate and ethyl acetate/methyl acetate mixture provided good octane numbers that were comparable to alcohols and ethers. Unfortunately, the water miscibility of these esters was too high. Thus, the volume increase of the aqueous phase when a gasoline fuel was shaken with water gave about 20% partitioning of ethyl acetate into the water phase (ethanol partitioning is 100%), which is unacceptable particularly for fuel pipeline transport. Thus, a low production cost and lower water miscibility of the ester oxygenates are desired.

Objects

It is an object of the present invention to provide oxygenates for improving the fuel without adversely affecting its stability and emission characteristics and without the current negative health and environmental hazards associated with current oxygenates. It is also an object to provide a reliable low cost process for manufacturing these oxygenates, which requires a relatively low capital investment and relatively little operator attention. Oxygenation of the fuel offers the possibility of reducing particulate matter emissions significantly, and as such, it is of significant practical interest and value to society. It is further apparent that the future use of oxygenated fuels is inevitably tied to environmental improvement efforts. Although the blending of MTBE and alcohols in fuels for octane improvement or supply extension with improved profitability will also continue, the need for alternative biodegradable oxygenates is clear.

SUMMARY OF THE INVENTION

The present invention relates to a method of producing an oxygenated fuel comprised of alkyl esters and alkyl diesters from lower alkyl, containing 1 to 8 carbon atoms, esters of fatty acids or free fatty acids comprising: (a) combining the lower alkyl esters, or free fatty acids, with an alcohol containing 1 to 8 carbon atoms, and an alkaline catalyst to provide a reaction mixture; (b) exposing the reaction mixture to ozone to cleave double bonds in the acids or esters to provide terminal ends which react with the alcohol; and (c) separating the alkaline catalyst and any unreacted amounts of the alcohol from the reaction mixture to provide the oxygenated fuel.

The present invention also relates to a method wherein the alkyl esters or free fatty acids are selected from the group consisting of vegetable oils, greases, animal fats, rendered fats and oils and mixtures thereof.

The present invention also relates to a method wherein the alcohol is selected from the group consisting of methanol, ethanol, propanol, isopropanol, 1-butanol, benzylic alcohol, 2-butanol or isobutanol and mixtures thereof.

The present invention also relates to a method wherein the reaction mixture further comprises a non-reactive solvent. Preferably, the invention relates to the method wherein the alkaline catalyst is a metal hydroxide base, alkaline earth oxide or an amine. Further, the present invention relates to a method wherein said reaction mixture is exposed to ozone for sufficient period of time to cleave more than 50% of the double bonds. Still further, the present invention relates to a method wherein the process is maintained at a temperature of between about −30° C. to about 60° C.

The present invention relates to a method wherein the oxygenated fuel is more volatile and its molecular weight is lower than the esters of fatty acids or free fatty acids. Still further, the present invention relates to a method wherein the fuel is more thermally stable and oxygen resistant than the esters of the fatty acids or free fatty acids. Further still, the present invention relates to a method wherein the oxygenated fuel is mixed in a diesel fuel in amounts up to about 20% (v/v) based on the fuel.

The present invention relates to a composition comprising a mixture of diesel fuel containing from about 0.5-75 wt. % of the oxygenated fuel of Claim 1.

The present invention is particularly directed at a method for improving the cetane number of a middle distillate fuel by catalytic ozonation of fatty esters by selectively cleaving the double bonds of the unsaturated fatty acid and converting them to oxygenated ester compounds. In one (1) preferred embodiment, methyl soyate is selectively oxygenated. The resulting oxygenated stream may be used as a diesel fuel alone, or it may be blended with other petroleum streams to produce a middle distillate stream having an acceptable cetane rating.

In another preferred embodiment, the oxygenated esters and diesters mixture produced from the catalytic ozonation is separated into a first fraction relatively rich low molecular weight compounds, and into a second fraction relatively rich in higher boiling point oxygenated compounds. Any of these oxygenated fractions may be used alone or may be blended with other petroleum streams to produce a middle distillate having an improved cetane number.

This invention provides a process wherein all or at least a potion of the oxidation product of the process consists essentially of materials boiling between about 50° C. and 425° C. Preferably, the oxygenates mixture consisting essentially of material boiling between about 150° C. and about 400° C., and more preferably boiling between about 175° C. and about 375° C. According to further aspects of this invention, the boiling point range of the product mixture is controlled by the particular conditions of the catalytic ozonation process and the reaction time. Advantageously, the oxygenate product mixture can be made free of unsaturation.

Thus, the present invention is targeted at the preparation and use of a novel family of oxygenated compounds in diesel fuels which make it possible to increase the cetane number and to introduce greater flexibility into the formulation of diesel fuels for a lower cost. In addition, the novel oxygenates in this invention are derived from fatty esters and are non-toxic and biodegradable.

The substance and advantages of the present invention will become increasingly apparent by reference to the following description.

DESCRIPTION OF THE PREFERRED EMBODIMENTS

The oxygenate mixtures of the invention are generally prepared by contacting ozone gas with fatty acids or fatty ester in the presence of alcohol radicals and an alkaline catalyst under appropriate conditions for unsaturated bonds in the acids or esters to cleave and add to the alcohol at the new terminal chain ends produced by the reaction with ozone.

The use of ozone to cleave double bonds is well known to those skilled in the art. Ozone is a very powerful oxidation agent and it readily attacks and cleaves double bonds in alkenes. Aside from its high oxidation potential, ozone oxidation is convenient since unreacted ozone simply decomposes back to oxygen and no special neutralization or separation are required at the end of the reaction. Furthermore, since ozone is being produced "on site" it does not require complex logistics in transport, storage and disposal as many other oxidation agents. However, unlike uncatalyzed ozonation that yields a mixture of aldehydes and ketones functional radicals, the alkaline catalyzed ozonation process, in accordance with our invention, results in the formation of ester linkages between the alcohol and the new chain ends of the cleaved double bonds.

Any fatty acids or fatty ester containing unsaturation in their structure, either individually or as mixtures can be used. Usually, these fatty acids and fatty esters are derived from vegetable oils. Examples of such oils include, but are not limited to, soybean oil, safflower oil, linseed oil, corn oil, sunflower oil, olive oil, canola oil, sesame oil, cottonseed oil, palm oil, peanut oil, coconut oil, rapeseed oil, tung oil castor oil, fish oil, or and any mixture thereof. Additionally, any partially hydrogenated vegetable oils or genetically modified vegetable oils can also be used. Examples of partially hydrogenated vegetable oils or genetically modified vegetable oils include, but are not limited to, high oleic safflower oil, high oleic soybean oil, high oleic peanut oil, high oleic sunflower oil and high erucic rapeseed oil (crambe oil). The iodine values of these vegetable oils range from about 40 to 240 and more preferably from about 80 to 240. When vegetable oils having lower iodine values are used, oxygenates with lower oxygen content are obtained.

Preferable, hydroxyl compounds as alcohols containing 1 to 8 carbon atoms, which are employed to prepare the oxygenates are organic compounds having at least 1 active hydroxyl radical. Preferable compounds include but are not limited to methanol, ethanol, propanol, isopropanol, 1-butanol, benzylic alcohol, 2-butanol or isobutanol and the like. Particularly suitable are low molecular weight alcohols such as methanol and ethanol.

The catalysts used in preparing the oxygenate mixtures of this invention are solid or liquid alkaline compounds. Examples of such catalysts include, but are not limited to, alkali metal hydroxides (such as LiOH, NaOH, KOH and CsOH), organic amines (such as butyl amine, diethyl amine, pyridine, or 4-dimethylamino-pyridine), various salts derived from a strong base and a weak acid (such as sodium carbonate, calcium carbonate and magnesium carbonate), compounds composed of metal oxides having alkaline surface (such as BaO, MgO). The salt catalysts may be prepared by contacting the appropriate ratio of a strong base such as calcium hydroxide with a $C_{6-10}$ carboxylic acid and bubbling carbon dioxide through the mixture to form carbonate moieties. The catalysts suitable for this invention can either be soluble in the reaction mixture, known in the art as homogeneous catalyst or it can be dispersed as fine particles known as heterogeneous catalyst.

The concentration of the catalyst depends on the alkalinity of the particular catalyst used and the experimental conditions of the reaction. Thus, provided that a soluble and strong alkaline catalyst like NaOH is used, a concentration of 0.1 to 1.0 wt. % is sufficient when the reaction temperature is between 0° C. and 25° C., an ozone/oxygen flow rate of 0.25 ft$^3$/min. is used and the concentration of ozone in the gas atmosphere is about 6% by weight. When a heterogeneous catalyst is used, the average particle size and the particle size distribution must also be considered as smaller particles provide a higher total surface area than identical concentrations of the catalyst with larger particles. The amount of catalyst is therefore adjusted to provide maximum formation of ester linkages between the alcohol radicals and the new chain ends that are formed as a result of the cleavage of the double bonds as a result of the ozone attack.

Soluble (homogeneous) catalysts are neutralized at the end of the reaction with an acid base such as acetic acid, carbon dioxide and the salt is then separated from the product by washing with water and separating the desired oil phase from the water phase. When heterogeneous catalyst is used and it is dispersed in the reaction mixture as fine particles or present as a separate phase, the product is purified simply by filtration of the catalyst phase and removing it from the reaction product. In this case, the recovered catalyst can be reused.

Solvent or dispersant are not needed but can be used to control the viscosity of the reaction mixture or to enhance the compatibility of the various components in the reaction mixture. Such solvents or dispersants can be mineral spirits, silicone oil or chlorinated organic compounds commonly used in ozonolysis reactions. Preferably, the solvent should be stable to ozone and should not contain unsaturation. In a preferred embodiment, no solvent or dispersant is used.

The catalytic ozonation reaction can be run between about −30° C. and 60° C. More preferably, the reaction temperature is at approximately room temperature. During the introduction of ozone, the temperature of the reaction may rise and therefore, cooling must be applied. The extent to which the temperature rises depends upon the rate of the reaction, the temperature of the ozone/gas mixture, and the presence of solvent. The temperature can be controlled and maintained by contacting the reaction vessel with ice, coolant, or any other cooling methods familiar to the person expert in the art. It is preferable to maintain the reaction temperature close to 0° C. for safety and a balance between the solubility of ozone in the reaction medium and the rate of the reaction.

In a typical process, ozone is produced by passing dry oxygen (0.25 ft$^3$/min) through an ozone generator (Praxair Trailigaz generator model number OZC-1001) set up to yield about 6 wt. % ozone in oxygen. This ozone/oxygen atmosphere is introduced into the reaction medium as small gas bubbles by passing the gas stream through a fritted disc having fine pores. The formation of these small gas bubbles improved the dispersion of ozone within the reaction medium. The dispersion of the fine gas bubbles is further improved by stirring the reaction mixture using a mechanical stirrer equipped with appropriate stirrer. Any unreacted ozone that escaped from the reaction without reacting with the oil is destroyed by venting it through an exhaust outlet and into an aqueous potassium iodide solution.

EXAMPLES

This method for making biobased oxygenates is illustrated in the following Examples. These Examples are not meant in any way to limit the scope of this invention.

Example 1

Methyl soyate (15 g), methanol (60 mL), triethylamine (3 g), and dichloromethane (120 mL) were added to a reaction vessel equipped with a glass tube that was tipped with a fritted glass disk. The reaction mixture was cooled to about −75° C. by immersing the reaction vessel into a dewar surrounded by a dry ice/propanol bath. Ozone was produced by passing oxygen through a Praxair Trailigaz OZOBLOC Model OZC-1001 ozone generator (Cincinnati, Ohio). The concentration of ozone in the feed gas was maintained within the range of 6-10 wt %. The pressure of the generator was operated at about 83 KPa. The exit port of the ozone generator was connected with Tygon tubing to the inlet of the glass tube, and the gaseous oxygen/ozone mixture was delivered to the reaction mixture through the fritted disk at a flow rate of 165 cm3/s. The exhaust outlet was connected to a potassium iodide aqueous solution trap, in which excess ozone was rapidly decomposed. After 30 min. reaction time, the generator was shutdown and the reactor was flushed for 10 min with oxygen to remove excess ozone. The mixture was allowed to warm to room temperature, and dichloromethane was evaporated under a vacuum at 40° C. The solution was transferred to a separatory funnel, triethylamine was neutralized with a 2 M hydrochloric acid aqueous solution and the aqueous layer was discarded. Trace unreacted methanol that did not dissolve in the aqueous phase was removed by heating the organic phase under vacuum at 60° C. The oxygenate product mixture was dried over anhydrous calcium sulfate and filtered and characterized by GS-MS and FTIR. The results indicated complete cleavage of the double bonds and the formation of the desired methyl and dimethyl esters: dimethyl malonate, methyl hexanoate, methyl nonanoate, dimethyl azelate, and methyl myristate. In addition, small amounts of methyl linoleate, methyl linolenate and methly oleate were also present from incomplete cleavage of the double bonds by the ozone. Additionally, methyl palmitate and methyl stearate, which do not contain unsaturation, were also present in the reaction product. The GC-MS chromatograph further showed the presence of small quantities of 1,1-dimethoxyhexane, methyl octanoate, 1,1-dimethoxynonane, nonanal, methyl heptadecanoate, 9-(oxo)-methyl nonanoate, and methyl isocanoate, which most likely have been produced by side reactions.

Example 2

Methyl soyate (15 g), methanol (60 mL), and triethylamine (120 g) were added to a reaction vessel equipped with a glass tube that was tipped with a fritted glass disk and the reaction mixture was cooled in an ice/water bath to a constant temperature of 0° C. Ozone was introduced as described in Example 1. After 30 min. reaction time, the generator was shutdown and the reactor was flushed for 10 min. with oxygen to remove excess ozone. The product mixture was allowed to warm to room temperature, triethylamine was neutralized with a 2 M hydrochloric acid aqueous solution and the aqueous layer was discarded. Trace unreacted methanol that did not dissolve in the aqueous phase was removed by heating the organic phase under vacuum at 60° C. The oxygenate product mixture was dried over anhydrous calcium sulfate and filtered and characterized by GS-MS and FTIR.

Example 3

Methyl soyate (50 g), methanol (200 mL) and $CaCO_3$ (20 gr) were added to a reaction vessel equipped with a glass tube that was tipped with a fritted glass disk and the reaction mixture was cooled in an ice/water bath to a constant temperature of 0° C. Ozone was introduced as described in Example 1. After 90 min. reaction time, the generator was shutdown and the reactor was flushed for 10 min. with oxygen to remove excess ozone. The product mixture was allowed to warm to room temperature, triethylamine was neutralized with a 2 M hydrochloric acid aqueous solution and the aqueous layer was discarded. Trace unreacted methanol that did not dissolve in the aqueous phase was removed by heating the organic phase under vacuum at 60° C. The oxygenate product mixture was dried over anhydrous calcium sulfate and filtered. The product mixture was then characterized by GS-MS and FTIR. It was found that the product distribution was similar to that obtained in Example 1. The results further indicated almost complete cleavage of the double bonds and the formation of the desired new metyl esters and diesters.

Example 4

Methyl soyate (15 g), methanol (60 mL), and triethylamine (120 g) were added to a reaction vessel equipped with a glass tube that was tipped with a fritted glass disk and the reaction mixture was cooled in an ice/water bath to a constant temperature of 0° C. Ozone was introduced as described in Example 1. Samples were taken after 40, 60, 80, 100 and 120 min. reaction times. Each of these samples was then allowed to warm to room temperature, triethylamine was neutralized with a 2 M hydrochloric acid aqueous solution and the aqueous layer was discarded. Trace unreacted methanol that did not dissolve in the aqueous phase was removed by heating the organic phase under vacuum at 60° C. The oxygenate product mixture was dried over anhydrous calcium sulfate and filtered and characterized by GS-MS and FTIR. The formation of the oxygenated species as a function of reaction time is shown in Table 1:

TABLE 1

Concentration of oxygenates as a function of ozonation time

| Component | 0 min | 40 min | 60 min | 80 min | 100 min | 120 min |
|---|---|---|---|---|---|---|
| Dimethyl Malonate | 0 | 0.002 | 0.003 | 0.004 | 0.005 | 0.008 |
| Methyl Hexanoate | 0 | 0.029 | 0.031 | 0.047 | 0.067 | 0.104 |
| Methyl Nonanoate | 0 | 0.025 | 0.027 | 0.043 | 0.062 | 0.099 |
| Dimethyl Azelate | 0 | 0.050 | 0.084 | 0.100 | 0.128 | 0.197 |
| Methyl Palmitate | 0.924 | 0.948 | 1.027 | 0.937 | 0.907 | 1.004 |
| Methyl Linoleate and Methyl Linolenate* | 3.307 | 1.110 | 1.107 | 0.979 | 0.418 | 0.186 |
| Methly Oleate | 0.483 | 0.483 | 0.480 | 0.444 | 0.230 | 0.130 |
| Methyl Stearate | 0.299 | 0.274 | 0.316 | 0.298 | 0.241 | 0.298 |

(*Methyl linoleate and methyl linolenate could not be separated in the GC column)

It is intended that the foregoing description be only illustrative of the present invention and that the present invention be limited only by the hereinafter appended claims.

We claim:

1. A method of producing an oxygenated fuel comprised of alkyl esters and alkyl diesters from lower alkyl, containing 1 to 8 carbon atoms, esters of fatty acids or free fatty acids comprising:
   (a) combining the lower alkyl esters, or free fatty acids, with an alcohol containing 1 to 8 carbon atoms, and an alkaline catalyst to provide a reaction mixture;
   (b) exposing the reaction mixture to ozone to cleave double bonds in the acids or esters to provide terminal ends which react with the alcohol; and
   (c) separating the alkaline catalyst and any unreacted amounts of the alcohol from the reaction mixture to provide the oxygenated fuel.

2. The method of claim 1 wherein the alkyl esters or free fatty acids are selected from the group consisting of vegetable oils, greases, animal fats, rendered fats and oils and mixtures thereof.

3. The method of claim 1 wherein the alcohol is selected from the group consisting of methanol, ethanol, propanol, isopropanol, 1-butanol, benzylic alcohol, 2-butanol or isobutanol and mixtures thereof.

4. The method of claim 1 wherein the reaction mixture further comprises a nonreactive solvent.

5. The method of claim 1 wherein the alkaline catalyst is a metal hydroxide base, alkaline earth oxide or an amine.

6. The method of claim 1 wherein said reaction mixture is exposed to ozone for sufficient period of time to cleave more than 50% of the double bonds.

7. The method of claim 1 wherein the process is maintained at a temperature of between about −30° C. to about 60° C.

8. The method of claim 1 wherein oxygenated fuel is more volatile and its molecular weight is lower than the esters of fatty acids or the free fatty acids.

9. The method of claim 1 wherein the fuel is more thermally stable and oxygen resistant than the esters of the fatty acids or the free fatty acids.

10. The method of claim 1 wherein the oxygenated fuel is mixed in a diesel fuel in amounts up to about 20% (v/v) based on the fuel.

* * * * *